United States Patent
Schwarzmaier

[11] Patent Number: 5,861,020
[45] Date of Patent: Jan. 19, 1999

[54] APPARATUS FOR IRRADIATING BODY TISSUE WITH LASER LIGHT

[76] Inventor: Hans-Joachim Schwarzmaier, Auf'm Grossenfeld 7, Dusseldorf, Germany, D-40229

[21] Appl. No.: 849,370
[22] PCT Filed: Nov. 23, 1995
[86] PCT No.: PCT/EP95/04629
§ 371 Date: Jun. 6, 1997
§ 102(e) Date: Jun. 6, 1997
[87] PCT Pub. No.: WO96/17655
PCT Pub. Date: Jun. 13, 1996

[30] Foreign Application Priority Data

Dec. 9, 1994 [DE] Germany .................. P4443964.4

[51] Int. Cl.⁶ .................................................. A61N 5/00
[52] U.S. Cl. .................... 607/89; 607/93; 606/16
[58] Field of Search ............... 606/2, 10, 12–18; 607/88, 89, 92, 93

[56] References Cited

U.S. PATENT DOCUMENTS

| | | | |
|---|---|---|---|
| 4,383,729 | 5/1983 | Suzuki et al. | 606/15 |
| 4,718,417 | 1/1988 | Kittrell | |
| 4,799,479 | 1/1989 | Spears | 606/15 |
| 5,041,109 | 8/1991 | Abela | 606/15 |
| 5,151,096 | 9/1992 | Khoury | 606/17 |
| 5,207,669 | 5/1993 | Baker et al. | 606/15 |
| 5,219,346 | 6/1993 | Wagnieres et al. | 606/17 |
| 5,344,419 | 9/1994 | Spears | 606/15 |
| 5,415,655 | 5/1995 | Fuller et al. | 606/17 |
| 5,695,493 | 12/1997 | Nakajima et al. | 606/13 |

FOREIGN PATENT DOCUMENTS

| | | |
|---|---|---|
| 0 439 629 | 8/1991 | European Pat. Off. |
| 0 495 443 | 7/1992 | European Pat. Off. |
| 0 620 459 | 10/1994 | European Pat. Off. |
| 0 629 380 | 12/1994 | European Pat. Off. |
| 41 37 983 | 6/1992 | Germany. |
| 42 13 053 | 10/1993 | Germany. |
| WO 93 15677 | 8/1993 | WIPO. |
| WO 9315672 | 8/1993 | WIPO. |
| 93 20469 | 10/1993 | WIPO. |

Primary Examiner—John P. Lacyk
Assistant Examiner—Bryan K. Yarnell
Attorney, Agent, or Firm—McCormick, Paulding & Huber

[57] ABSTRACT

In an apparatus used to irradiate body tissue with high-intensity laser light, a probe with at least one waveguide is used which can be coupled with a laser light source and which at its light-exiting section, which can be inserted in the body tissue, is equipped with a diffuser element which consists of a base material that is highly transparent to the laser light and, dispersed therein, scattering particles that deflect the light rays, and with a first cover tube that surrounds the waveguide at a distance, that connects to a coolant source, that is open at its distal end and that, at least in the region of the diffuser element, is made of a transparent and good heat-conducting material, a device for modifying beam intensity is situated in the path of the laser beam before the input coupling point, with the waveguide in the region of the light-exiting section being surrounded by a reflector and/or absorber that has at least one light outlet in the region of the target radiation surface.

24 Claims, 4 Drawing Sheets

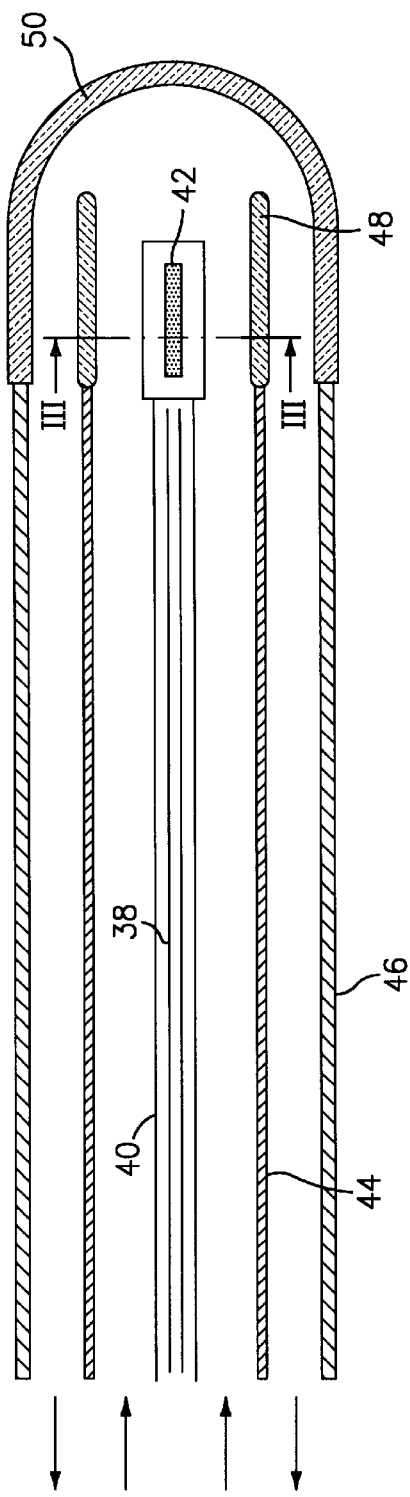
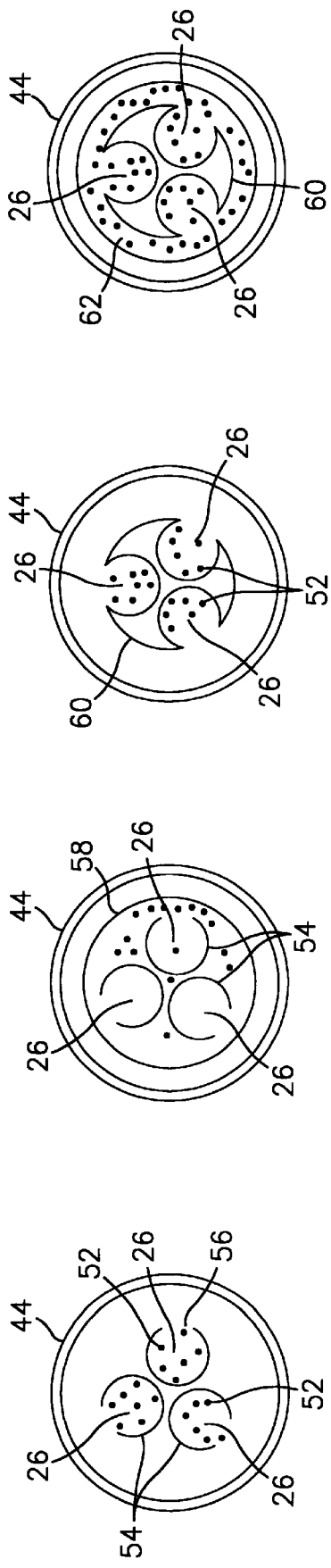

APPARATUS FOR IRRADIATING BODY TISSUE WITH LASER LIGHT

The invention relates to a device for irradiating body tissue with high intensity light, the device including a probe with at least one waveguide couplable with a laser light source on whose light exit section (which is insertable into body tissue) a diffuser element is provided which consists of a base material highly transparent for the laser light and scattering particles dispersed in this which deflect the light rays, and with a first cover tube surrounding the waveguide at a distance which can be connected with a coolant source, which is open at its distal end, and which consists of a transparent and good heat conducting material.

BACKGROUND OF THE INVENTION

The laser has been used since 1983 for interstitial heating of biological tissue. In the meantime, various probes and applicators have been developed to irradiate laser light into human tissue. Corresponding devices are described in German patent applications open to public inspection 38 13 227, 41 37 983, 42 13 053 and 42 21 364.

The previously described systems are constructed according to one more or less similar principle. The laser light is launched into an optical element located in the tip of the waveguide through a waveguide. Here as a rule it is a question of mirrors or prisms as well as special diffusers which permit an even irradiation of the laser light in all directions of space. These systems are provided in part with a cooling circuit for an additional modification of the temperature area profile, as this is, for example, described in DE-A-42 21 364, from which the preamble of claim 1 proceeds. A main problem of all interstitial heating procedures is, however, the exact adaptation of the temperature area profiles to the given tissue lesion. This will be sketched briefly with reference to the example of prostatic hyperplasia.

The prostate is divided anatomically into a right and a left prostate lobe as well as a median lobe. The geometrical extension is indeed similar in a normal prostate, apart from differences in size. The intensities of pathological changes are, however, extraordinarily different from patient to patient. In addition to a general enlargement of the prostate, there are also found isolated changes in the right or left prostate lobes as well as in the median lobe. Moreover, of course, very different combinations of these pathological changes can occur in individual cases. In addition to this, it frequently results that the target tissue reacts differently to laser radiation although the irradiation profile was adapted to the lesion. The temperature distribution can thus assume undesirably excessively high or, however, even too low temperatures during the irradiation. A similar problem emerges in connection with irregularly formed tumors, whereby especially the histological composition within the tumor (living cells, necroses, hemorrhages, vessels) can supervene in an aggravating manner. A laser probe which solves this problem has not been described until now.

SUMMARY OF THE INVENTION

A probe for irradiating body tissues with laser light is known from EP-A-439 629, which for achieving a uniform irradiation has a diffuser element and in which a reflector with light exit openings so surrounds the waveguide in the region of its light exit section that light preferably is emitted in the forward direction.

Underlying the invention is the object of constructing a device of the type named at the beginning such that it can be used in connection with a great number of specific pathological anatomical lesion shapes and permits an online adaptation of the laser output to various reactions within the irradiated tissue during the irradiation process.

This object is accomplished by arranging an installation in the path of the laser beam before the launching point for changing the beam intensity, and the waveguide is enclosed by a reflector and/or absorber in the area of its light exit section which has at least one light exit opening in the area of the desired radiation surface.

A first basic feature of a preferred embodiment of the solution of the invention concerns the launching of the laser light into the probe as well as the waveguide within the same. In contrast with known systems, the laser beam is split into the required number of component beams by means of a beam-splitting arrangement. Alternatively to or supplemental to this, the laser light source can have a multiplicity of individual lasers. Only then is the laser light launched into the probe which includes several waveguides. In accordance with a further essential feature, a facility for changing the radiation intensity is inserted between the beam-splitting arrangement and the probe per component beam which can be regulated continuously with, for example, the aid of a stepper motor.

The individual waveguides end on the tissue side, that is, on the distal end of the probe in a diffuser element which consists of a base material in an inherently familiar manner which is highly transparent for the laser light used. A defined number of scattering particles is introduced into this material. As an essential feature, however, the individual diffusers are encapsulated in accordance with the invention with a highly reflective material, whereby the reflector so constructed has an opening solely in the area of desired irradiation. Here it must in particular be pointed out that a redirection of the beam with the aid of a prism or mirror in the light exiting area does not suffice for an effective irradiation. The beam must rather be as homogeneously distributed as possible over the entire exit area, as the high power densities otherwise occurring lead to an overheating of the tissue near the probe. On the other hand, however, a diffuser (even with asymmetrical distribution of the scattering particles, as described, for example, in DE-OS 42 21 364) without reflecting jacketing is not sufficiently suited to prevent light exiting in an undesired direction completely. With the solution of the invention, the reflector enclosing the diffuser ensures that light from the respective waveguide is only radiated in the desired direction. In this way, the direction and intensity of the radiated laser light can be selected in accordance with the respective shape of the tissue to be irradiated. The number of radiation elements is chosen corresponding to the application in question.

The measures for modifying the initial photon distribution in the tissue are nevertheless taken by themselves unsuited for solving the problem, as a symmetrical lesion arises again owing to temperature conduction in the tissue despite asymmetrical irradiation. Only cooling the tissue near the probe through the probe guarantees the asymmetrical lesion, as through this the temperature gradient created by light absorption remains preserved in the tissue, and a temperature equilibrium between irradiated and not irradiated tissue areas is prevented. In addition, the cooling circuit serves for additional modification of the temperature area profile.

The online regulation of the laser-tissue interaction requires an adequate temperature monitoring. According to the construction of the device, the probe is therefore additionally provided with at least a temperature sensor, for example a thermocouple.

Spot temperature measurements are as a rule insufficient, with asymmetrical temperature area profiles. This holds especially for indications in connection with which, owing to tissue inhomogeneity, varying temperature courses are to be expected. Here a three dimensional temperature monitoring is necessary for an indicative temperature measurement. Monitoring the irradiation process with the aid of nuclear spin tomography represents a practicable solution. The whole body spooling used at this time, however, is limited with respect to its resolution of detail, for example the urethral wall.

In accordance with a preferred embodiment of the invention, the probe, therefore, includes an additional antenna for direct local application of the high frequency radiation necessary for diagnosis by means of usual nuclear spin tomography. In addition, the antenna can also be connected as a receiving antenna, or an additional receiving antenna can be provided to receive the high frequency radiation emitted by the nuclear spin tomograph. This antenna can also be used for application of therapeutic radiation doses.

Other advantageous configurations of the invention are indicated in the claims.

BRIEF DESCRIPTION OF THE INVENTION

Further features and advantages of the invention emerge from the following description which explains the invention on the basis of embodiments in connection with the appended drawings. Depicted are:

FIG. 1 A schematic representation of the part of the device connected with the proximal end of the probe with a laser light source, a beam-splitting arrangement and a heat exchange installation, FIG. 2 A schematic section containing the axis through the distal end region of the probe, FIGS. 3 to 6 Schematic cross sections through the probe along the line III—III in FIG. 2, whereby the outer cover tube of the probe is not represented, FIG. 7 A section representation corresponding to FIG. 2 through a probe in accordance with a second embodiment of the invention, FIG. 8 A section corresponding to FIGS. 3 to 6 through the second embodiment of the probe along line VIII—VIII in FIG. 7, FIG. 9 A schematic representation of the practical use of the probe in irradiation of the prostate, and FIG. 10 A section along line X—X in FIG. 7.

DETAILED DESCRIPTION OF THE PREFERRED EMBODIMENTS

Figure 1:
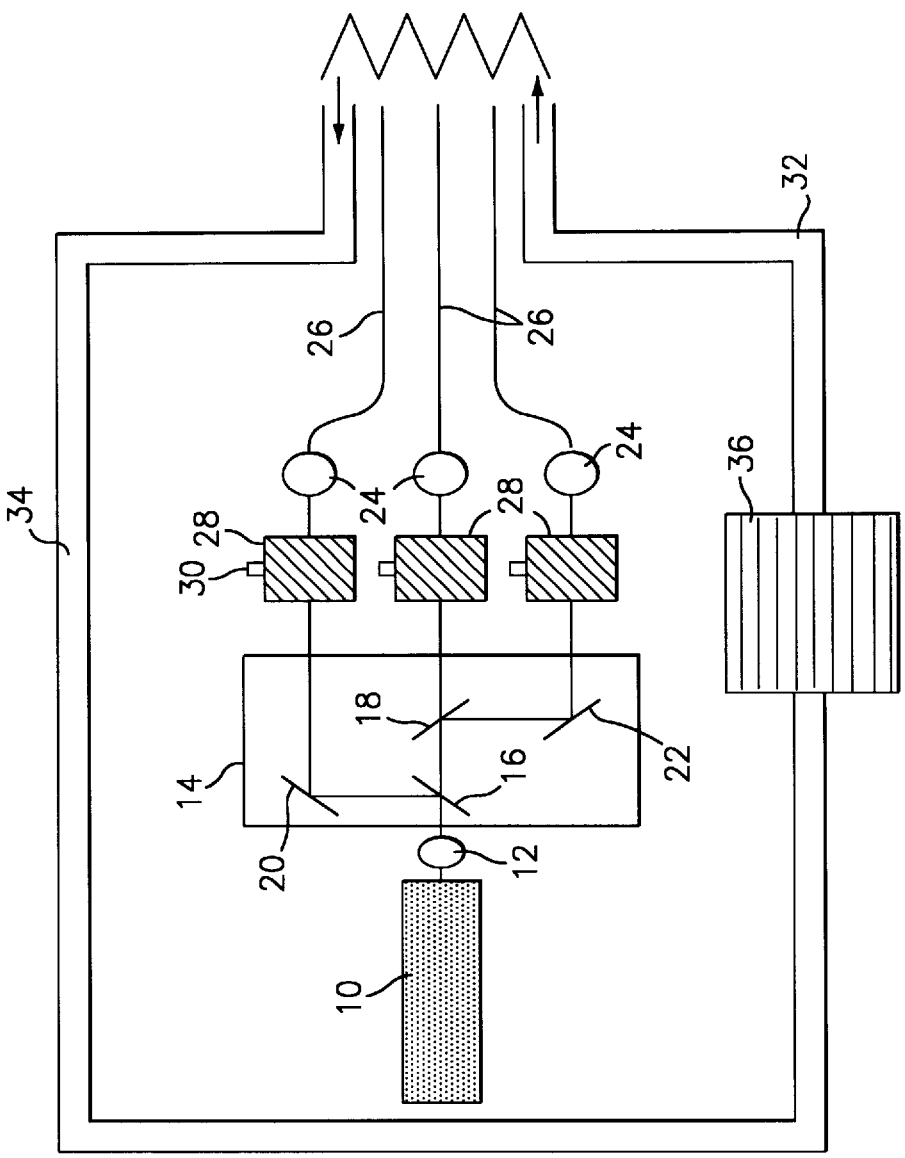

FIG. 1 illustrates a laser 10, the initial beam of which is launched into a beam-splitting arrangement 14 by means of an optical system 12. The beam-splitting arrangement here includes, for example, two beam splitters 16, 18 arranged one behind the other and two mirrors 20, 22 which break down the launched beam of the laser 10 into three component beams in the manner represented. The number of beam splitters must, of course, be varied according to the desired number of component beams. The component beams are at all times launched into one waveguide 26 each through an optical system 24. Between the exit of the beam-splitting arrangement 14 and the respective optical system 24, a facility for changing the intensity of the component beam is arranged in each component beam, for example, a variable filter 28. The attenuation of the beam can alternatively also take place with rotating mirror prisms or glass plates. The variable filter can, for example, be continuously regulated with the help of a stepper motor.

The device represented in FIG. 1 furthermore includes a cooling circuit to cool the probe with an inflow 32, an outflow 34 and a pump/heat exchange unit 36 for pumping and tempering the coolant.

The probe proper is connected to the device schematically represented in FIG. 1, the distal end section of which is represented in FIG. 2. An optical fiber bundle 38 consisting of the waveguides 26 which is appropriately enclosed by an additional casing 40 (for example, hose, tube) for better mechanical stability is located in the center of the probe to be introduced into the tissue. The waveguides or glass fibers 26 end distally in a radiating head which will be explained in greater detail on the basis of FIGS. 3 to 6. The fiber bundle 38 is enclosed at a radial distance by an inner first cover hose or cover tube 44, which is open at its distal end, and which forms the inflow 32 for the coolant. This inner cover tube is for its part enclosed at a radial distance by a second cover tube 46 which is closed on its distal end, and which forms the outflow or return for the coolant. The end section 48 of the inner cover tube which encloses the radiation head 42 and the corresponding cap-like closed end section 50 of the outer cover tube 46 are made of a material with good transparency for the laser radiation used in any given case. The material used for the transparent cup plug 50 must above and beyond this be a good heat conductor.

The radiation head 42 will now be explained in greater detail on the basis of FIGS. 3 to 6.

With the embodiment in connection with FIG. 3, each wave guide 26 ends in a diffuser 52. A combination of a highly transparent base material (methyl methacrylate or similar materials, glass or glass-like materials) and dispersed scattering centers (for example, barium sulfate, magnesium oxide and similar scattering substances, air bubbles or foam glass) is used as material for the diffuser. The diffuser is at all times partially enclosed by a highly reflective casing 54. The diffuser so encapsulated only has an opening 56 in the desired irradiation area. Any highly reflecting material (for example, gold, aluminum and the like) for the wavelength used comes into consideration for the capsule material.

With the embodiment represented in FIG. 4, the three partially encapsulated diffusers are dispersed as a whole in a diffuser 58. If need be, the inner diffusers 52 can be omitted with this solution.

With the embodiment represented in FIG. 5, the reflectors surrounding the individual diffusers 52 are enclosed by a single cylindrical element of a highly reflecting material which accommodates the waveguide end sections and the diffusers 52, and which again has corresponding openings 56 in the radiation area. Even this element 60 can be embedded in an external diffuser 62 as with the embodiment in accordance with FIG. 4, as FIG. 6 shows this. This permits a further modification of the temperature area profile to be attained with the probe.

The respective inner diffusers 52 and outer diffusers 58, 62 can be modified with respect to their scattering characteristics either by changing the scattering particles in the base material or, however, by a change in the form of the diffuser. A change in the form of the internal diffuser of course also requires a change in the form of the highly reflective casing or reflector.

As one recognizes, the scattered light is only emitted in certain directions owing to the reflectors 54, 60 provided in accordance with the invention partially enclosing the ends of the waveguides 26. In connection with a control of the intensity of the launched light through the filter element 28, the intensity and direction of the radiated laser light can consequently be controlled, and the radiation profile therewith be adapted to the lesion of the irradiated tissue.

Figure 10:
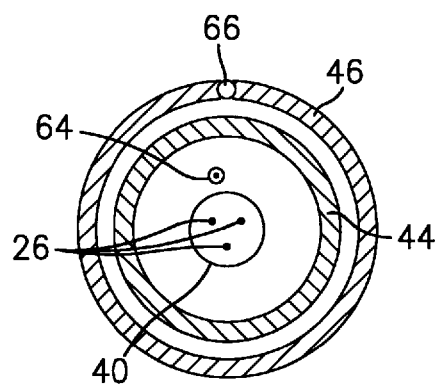

The circulating coolant permits a modification of the temperature area profile obtained by means of the irradiated energy. Monitoring the temperature area profile can take place through temperature measurements by means of one (temperature sensor 66 in FIG. 10) or several temperature probes, preferably with a nuclear spin tomograph. For this purpose, an antenna 64 is provided with the embodiment in accordance with FIG. 7 inside the inner cover tube 44 of the probe which makes possible a local irradiation of high frequency energy or a reception of the corresponding signals for nuclear spin tomographic monitoring. The antenna can also be used for simultaneous irradiation of therapeutic radiation doses of high frequency energy of suitable wave length (for example, 2.45 GHz), which permits an additional modification of the temperature area profile. The diffuser element is moreover constructed as with the embodiment in accordance with FIG. 3.

Figure 7:
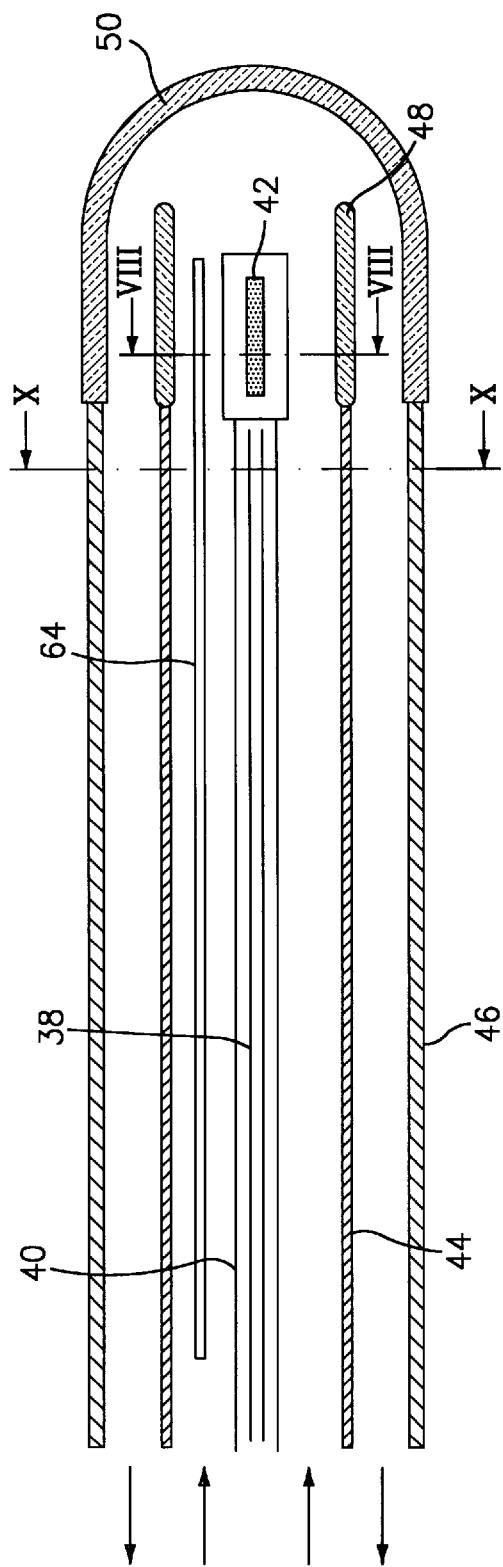
Figure 8:
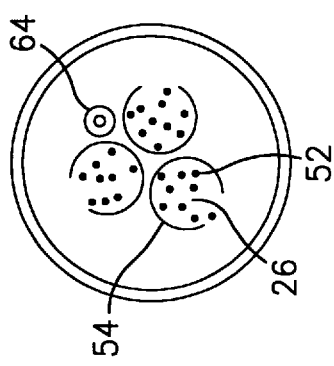

The cooling circuit can be variously constructed in modification of the embodiments represented in FIGS. 2 and 7. In accordance with a first variant, only a cover tube with transparent end cap is used, whereby the interstitial space between the optical fiber bundle 38 and the cover tube is separated by a horizontal membrane such that the upper part of the tube is constructed as an inflow and the lower part of the tube as outflow. With another variant, a liquid wave guide is used. By suitable selection of the liquid and waveguide, the inflowing liquid is directly used as waveguide. The radiating element must in this case be constructed porously if need be.

Figure 9:
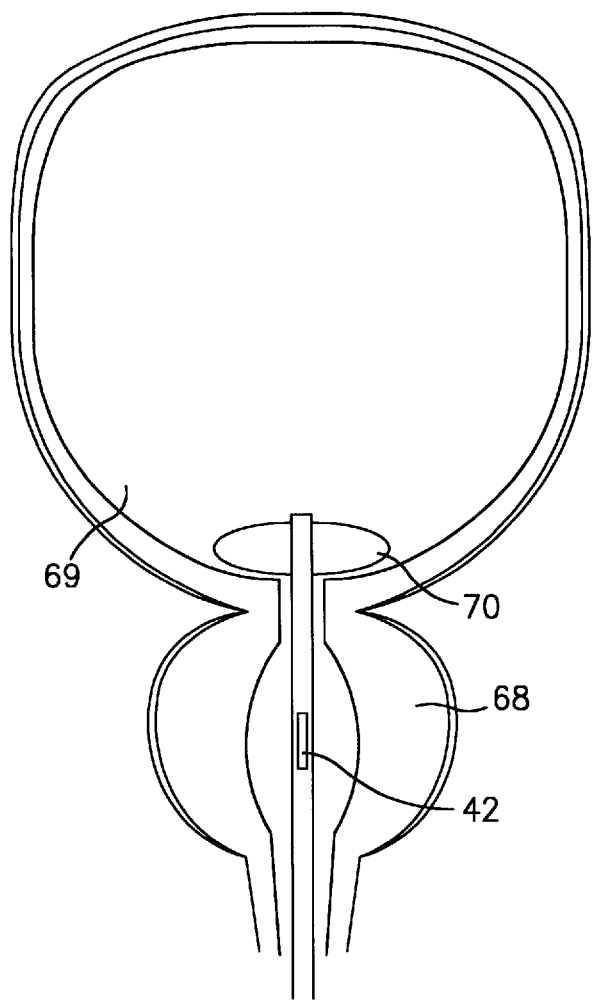

The probe can be variously constructed for adaptation to the anatomical particularities of its respective area of use. Thus, when using the probe in connection with the prostate, the radiating unit will not lie in the tip area as is the case with the embodiments in accordance with FIGS. 2 and 7. In accordance with FIG. 9, the radiating head 42 is positioned such that it lies within the prostate 69. The tip of the probe, however, can be advanced into the bladder 68. With such an embodiment, additional positioning aids are required if worse comes to worse, for example a balloon 70. This could be positioned either in the urinary bladder or, however, in the urethra itself. In connection with one construction variant, this balloon could also replace the outer casing of the probe. The outflow of the coolant would in this case take place between the inner cover tube and the positioning balloon, whereby this must then again have good transparency and be an adequate heat conductor for the laser light used.

With a further, not represented embodiment, one can also completely manage without the second casing in the area of the urethra when using a suitable positioning balloon. In this case, the urethra itself is used as outflow. This offers the advantage that the coolant directly cools the urethra. In this case, a further balloon is positioned further distally below the prostate in order to assure the irradiation shape. This has at its disposal a tube system in order to make the outflow of the coolant possible.

I claim:

1. Device for irradiating body tissues with laser light of high intensity, said device comprising a probe with a plurality of waveguides (26) each couplable with a respectively associated one of a plurality of laser beams from a laser light source (10), each of said waveguides having a light exit section insertable into body tissue provided with a diffuser element (52) which diffuser element consists of a base material highly transparent for the laser light and scattering particles dispersed in said base material which particles deflect the light rays, and a first cover tube (44) surrounding the waveguides (26) at a distance so that said first cover tube can be connected with a coolant source (36), said first cover tube having an open ended distal end portion surrounding said light exit sections of said waveguides and made of a transparent and heat conducting material, there being arranged in the path of each of said laser beams, in advance of the beam reaching its associated one of said waveguides, an installation (28, 30) for changing the intensity of the beam, and each waveguide (26) being enclosed at its light exit section by an element, selected from the class consisting of a reflector (54) and an absorber, which element has at least one light exit opening (56).

2. Device according to claim 1, wherein between the laser light source (10) and the waveguides (26) a beam-splitting device (14) is positioned for splitting the beam of the laser light source (10) into component beams.

3. Device according to claim 2, wherein the laser light source includes a number of individual lasers.

4. Device according to claim 2, wherein the beam-splitting arrangement (14) with more than two waveguides (26) includes a number of successive beam-splitting elements (16, 18).

5. Device according to claim 1, wherein the installation for changing the intensity of each beam for each one of said beams includes an arrangement for reflecting that one beam.

6. Device according to claim 1, wherein the installation (28, 30) for changing the irradiation intensity includes an absorption element (28).

7. Device according to claim 6, wherein the absorption element (28) is an optic light filter.

8. Device according to claim 1, wherein the light exit section of each waveguide (26) is embedded in its own diffuser element (52) which is enclosed by the reflector (54).

9. Device according to claim 1, wherein the element is jointly embedded in an external diffuser (58).

10. Device according to claim 1, wherein the reflectors (54) enclosing the light exit sections of the waveguides (26) are embedded in an external diffuser (58).

11. Device according to claim 1, wherein the reflectors are the partial cylindrical walls of borings which are constructed in a reflector element (60).

12. Device according to claim 1, wherein the base material for the diffuser (52, 58, 62) is chosen from the materials group comprising methyl methacrylate, glass and flexible transparent substances, and wherein the material for the scattering particles is selected from the materials group including barium sulfate, magnesium oxide and aluminum oxide.

13. Device according to claim 1, wherein the scattering particles in the diffusers consist of glass with a refraction index different from the base material or with glass inclusions.

14. Device according to claim 1, wherein the first cover tube (44) is surrounded at a distance by a second cover tube (46) to form an annulus between the two cover tubes (44, 46); said second cover tube being closed off in the light exit sections of the waveguides by a transparent cap (50) which conducts heat so that the first cover tube (44) can be connected to a coolant supply (32) and the annulus between the two cover tubes (44, 46) can be connected to a coolant outflow (34).

15. Device according to claim 1, wherein the waveguides (26) are constructed as liquid waveguides and connected to a coolant inflow from the coolant source.

16. Device according to claim 1, wherein the probe is provided with a positioning aid in the form of at least one balloon (70).

17. Device according to claim 16, wherein the positioning aid is situated adjacent said light exit sections and is transparent and a heat conductor.

18. Device according to claim 17, wherein the positioning aid (70) is arranged outside the light exit sections of said waveguides.

19. Device according to claim 1, having a rigid outer probe casing (46).

20. Device according to claim 1, having a flexible outer probe casing (46).

21. Device according to claim 1, wherein the probe has at least one temperature sensor.

22. Device according to claim 1, wherein the probe is manufactured of nuclear spin-compatible materials.

23. Device according to claim 1, wherein the probe is constructed in the form of a catheter having a distal end provided with a tip for insertion into solid tissue.

24. Device according to claim 1, wherein the probe has at least one antenna for the irradiation and/or receiving of high frequency energy.

* * * * *